(12) United States Patent
Villarreal, Jr. et al.

(10) Patent No.: US 11,571,370 B2
(45) Date of Patent: Feb. 7, 2023

(54) ANTIFUNGAL SOLUTION AND WIPE

(71) Applicant: PELLI SKIN CO., LLC, Mission, TX (US)

(72) Inventors: Jesse Villarreal, Jr., Mission, TX (US); Carolyn Shawn Murphy, Harrison, OH (US)

(73) Assignee: PELLI SKIN CO., LLC, Mission, TX (US)

( * ) Notice: Subject to any disclaimer, the term of this patent is extended or adjusted under 35 U.S.C. 154(b) by 180 days.

(21) Appl. No.: 17/170,375

(22) Filed: Feb. 8, 2021

(65) Prior Publication Data

US 2021/0161773 A1  Jun. 3, 2021

Related U.S. Application Data

(62) Division of application No. 16/299,454, filed on Mar. 12, 2019, now Pat. No. 10,993,890.

(60) Provisional application No. 62/782,550, filed on Dec. 20, 2018, provisional application No. 62/715,631, filed on Aug. 7, 2018, provisional application No. 62/643,627, filed on Mar. 15, 2018.

(51) Int. Cl.
| | |
|---|---|
| A61K 9/00 | (2006.01) |
| A61K 31/325 | (2006.01) |
| A61K 31/357 | (2006.01) |
| A61K 8/49 | (2006.01) |
| A61Q 17/00 | (2006.01) |
| A61K 8/46 | (2006.01) |
| A61K 8/9789 | (2017.01) |
| A61K 8/02 | (2006.01) |
| A61K 9/70 | (2006.01) |

(52) U.S. Cl.
CPC .............. *A61K 8/0208* (2013.01); *A61K 8/46* (2013.01); *A61K 8/4973* (2013.01); *A61K 8/9789* (2017.08); *A61K 9/0014* (2013.01); *A61K 9/7007* (2013.01); *A61K 31/325* (2013.01); *A61K 31/357* (2013.01); *A61Q 17/005* (2013.01)

(58) Field of Classification Search
CPC combination set(s) only.
See application file for complete search history.

(56) References Cited

U.S. PATENT DOCUMENTS

| | | |
|---|---|---|
| 6,224,887 B1 | 5/2001 | Samour et al. |
| 6,455,592 B1 | 9/2002 | Laugier et al. |
| 2006/0165747 A1 | 7/2006 | Rolf |
| 2007/0287675 A1 | 12/2007 | Hitt et al. |
| 2007/0292355 A1 | 12/2007 | Tamarkin et al. |
| 2009/0092576 A1 | 4/2009 | Trimble |
| 2010/0160273 A1 | 6/2010 | Friedman et al. |
| 2012/0196822 A1 | 8/2012 | Meyer et al. |
| 2014/0205559 A1 | 7/2014 | Capriotti et al. |
| 2016/0168203 A1 | 6/2016 | O'Neil |
| 2019/0282458 A1 | 9/2019 | Villarreal, Jr. et al. |

FOREIGN PATENT DOCUMENTS

| | | |
|---|---|---|
| WO | 9939680 A1 | 8/1999 |
| WO | 2008075207 A2 | 6/2008 |

OTHER PUBLICATIONS

International Search Report and Written Opinion, PCT/US2019/022286, dated Jun. 7, 2019.

*Primary Examiner* — Hasan S Ahmed
(74) *Attorney, Agent, or Firm* — Miller Nash LLP

(57) ABSTRACT

A wipe has a substrate, a treatment solution impregnated into the substrate, the treatment solution including an antifungal agent, an antifungal agent solvent, and a carrier fluid, wherein the treatment solution is essentially free of alcohol. A treatment solution, has an antifungal agent, an antifungal agent solvent, and a carrier fluid, wherein the treatment solution has an alcohol content of 6 wt % or below of the total solution.

13 Claims, 4 Drawing Sheets

ANTIFUNGAL SOLUTION AND WIPE

RELATED APPLICATIONS

This application is a divisional of U.S. patent application Ser. No. 16/299,454, filed Mar. 12, 2019, which is a continuation of and claims priority to U.S. Provisional Patent Application Nos. 62/643,627, filed Mar. 15, 2018; 62/715,631, filed Aug. 7, 2018; and 62/782,550, filed Dec. 20, 2018, which are incorporated herein by reference in their entirety.

TECHNICAL FIELD

This disclosure relates to an essentially alcohol-free, antifungal treatment solution for skin care, which may be in the form of a wipe, aerosol spray, spray, liquid, lotion or cream, as examples without limitation.

BACKGROUND

Over-the-counter antifungal treatments for the treatment and/or prevention of athlete's foot and other foot funguses generally take the form of creams or sprays. For sprays the antifungal ingredient usually consists of terbinafine hydrochloride, miconazole nitrate, or tolnaftate. The sprays all include alcohol used as a solvent to keep the active ingredients in solution so they can propel out of the container. The propellant may consist of isobutane, n-butane, and propane. Dimethyl ether (DME) may also be a propellant. The alcohol is also added to give the skin a "cooling" sensation and aid in skin permeation when applied. None of these materials are good for the skin.

The container often consists of an aerosol can. Alternatives to aerosol cans have several advantages. For example all the aerosol metal cans used to apply athlete's foot sprays are non-recyclable metal aerosol spray cans. These non-recyclable cans are an inefficient delivery system and not good for the environment.

Alternative forms of over-the-counter antifungal treatment exist in creams and powders. Foot creams often have the same ingredients as the sprays, minus the propellants and almost universally include alcohol. Another item to note is that many available over-the-counter foot creams use either terbinafine hydrochloride, tolnaftate, butenafine hydrochloride, or clotrimazole as the antifungal ingredient, referred to here as the active ingredient. Powders seem to be more directed to prevention rather than curing foot fungal infections. Many of the powders have no over the counter antifungal active ingredients at all. Some powders contain menthol, which is not a proven FDA antifungal but the powders list as their active ingredient.

Another issue that arises from the application of the active ingredients in the form of either sprays or creams. Typically, the instructions are first to clean, then to apply to the affected area such as in between the toes, or to apply to the toes to prevent infection. For powders, the instructions typically involve sprinkling the toes with the powder, or putting it in shoes or socks for prevention of athlete's foot. This delivery system does not make for efficient applications of the active ingredients. A better delivery system and more efficacious formula for antifungal treatments for the feet would be desirable.

DETAILED DESCRIPTION OF THE EMBODIMENTS

Figure 1:
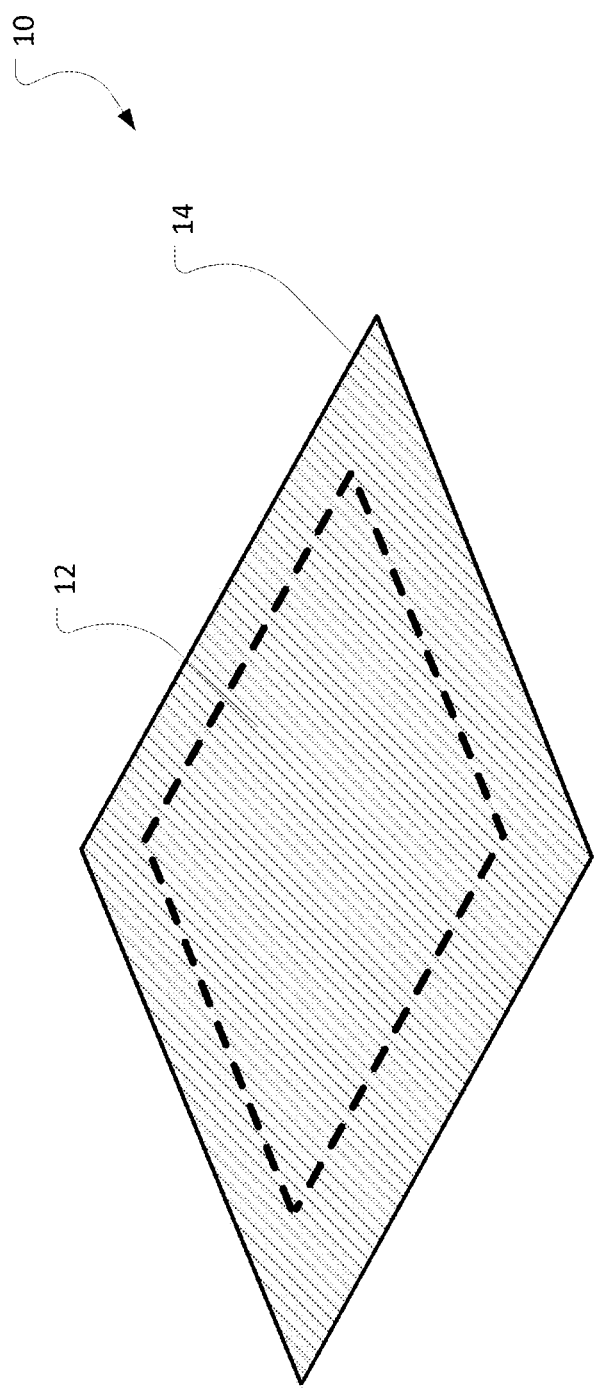
FIG. 1 shows one embodiment of an antifungal wipe substrate.

As used here, the term "treatment solution" means a solution comprised at least of an antifungal agent and a carrier fluid, which may also include an antifungal agent solvent. As used here, the term "antifungal agent" means any drugs, identified at least below, used to at least treat, and may treat and prevent, fungal infections, including athlete's foot, tinea pedis, ringworm, tinea capitis, and jock itch, tinea cruris. One should note that while much of the discussion focuses on athlete's foot, the application of the embodiments here is not limited to that particular fungal infection and should not be construed as such a limitation.

The embodiments here generally comprise an antifungal and soothing, healing solution that cleans, conditions, revitalizes and protects. As mentioned above, the treatment solution may contain several components, or it may consist only of a carrier fluid that carries the amount of antifungal agent needed. The US Food and Drug Administration requires that the antifungal ingredient be present in specific amounts. The following are drugs that have received the US FDA's approval as antifungals in its Final Monograph: tolnaftate 1%, clioquinol 3%; haloprogin 1%; miconazole nitrate 2%; povidone iodine 10%; undecylenic acid and its salts of calcium, copper and zinc, for a total undecylenate concentration of 10-25%; and clotrimazole 1%.

It is important to note, all the drugs listed are only approved for the treatment of athlete's foot and the relief of symptoms due to athlete's foot. However, only tolnaftate, a naphthyl thiocarbamate, is also approved for the prevention of athlete's foot. The above drugs contained within the FDA's Final Monograph are considered Generally Recognized As Safe and Effective (GRASE) for the treatment of athlete's foot. In addition, terbinafine hydrochloride received approval by the FDA as a treatment only for athlete's foot within the individually filed New Drug Application.

Other drugs that are used for the treatment of athlete's foot not contained within the Final Monograph by the FDA are: ketoconazole, an imidazole, (1-[4-(4-{[(2R,4S)-2-(2,4-Dichlorophenyl)-2-(1H-imidazol-1-ylmethyl)-1,3-dioxolan-4-yl]methoxy}phenyl)-1-piperazinyl]ethanone); sulconazole, an imidazole (1-{2-[(4-Chlorobenzyl)sulfanyl]-2-(2,4-dichlorophenyl)ethyl}-1H-imidazole); sertaconazole, an imidazole (1-{2-[(7-Chloro-1-benzothiophen-3-yl)methoxy]-2-(2,4-dichlorophenyl)ethyl}-1H-imidazole); betamethasone ((11β,16β)-9-Fluoro-11,17,21-trihydroxy-16-methylpregna-1,4-diene-3,20-dione)+clotrimazole, an imidazole (1-[(2-Chlorophenyl)(diphenyl)methyl]-1H-imidazole); ciclopirox (6-Cyclohexyl-1-hydroxy-4-methyl-2(1H)-pyridinone); econazole (1-{2-[(4-Chlorobenzyl)oxy]-2-(2,4-dichlorophenyl)ethyl}-1H-imidazole); naftifin ((2E)-N-Methyl-N-(1-naphthylmethyl)-3-phenyl-2-propen-1-amine); oxiconazole ((1Z)-N-[(2,4-Dichlorobenzyl)oxy]-1-(2,4-dichlorophenyl)-2-(1H-imidazol-1-yl)ethanimine); butenafine, a Trimethylamine, (N-Methyl-1-[4-(2-methyl-2-propanyl)phenyl]-N-(1-naphthylmethyl)methanamine); undecylenic acid+cholorozylenol (para-chloro-meta-xylenol). Any of these ingredients could be used in place of the tolnaftate, but they are only approved for the treatment and not the prevention of athlete's foot.

As used herein "an effective amount" for the antifungal agent means the amounts indicated in the FDA's Final Monograph for treatment and/or prevention of tinea infections, such as athlete's foot, jock itch, ringworm and related skin conditions. For antifungal agent not listed on FDA's Final Monograph, an amount of at least USP 1%-12% by weight of the solution should be utilized in the formulation.

The present formulation of the treatment solution contains an antifungal agent in an effective amount. The selected antifungal agent amounts may vary and should be within the amounts indicated by the FDA's Final Monograph or as defined herein. The antifungal agent can be for the treatment of tinea infections, it can be for the prevention of tinea infections or it can be for both treatment and prevention of tinea infections. The antifungal agent is selected from a naphthyl thiocarbamate active such as tolnaftate USP 1%, hydroxyquinolines such as clioquinol USP 3%; haloprogin (1,2,4-trichloro-5-(3-iodoprop-2-ynoxy)benzene) USP 1%; miconazole nitrate (1-[2-(2,4-dichlorophenyl)-2-[(2,4-dichlorophenyl)methoxy]ethyl]imidazole; nitric acid) USP 2%; povidone iodine (1-ethenylpyrrolidin-2-one; iodine) USP 10%; undecylenic acid and its salts USP 10-25%; and imidazole antifungal agents include sulconazole nitrate, econazole nitrate, miconazole nitrate and clotrimazole (1-[(2-chlorophenyl)-diphenylmethyl]imidazole) USP 1%.

The treatment solution contains a carrier fluid. The carrier fluid is essentially free of alcohols. As used herein, "alcohols" means SD alcohol, denatured alcohol, isopropyl alcohol, ethanol and mixtures thereof. As used herein "essentially free of" means that alcohols are not intentionally included in the present formulation, such as being present less than 1 wt % of the treatment solution. Alcohols may be carrier materials for other materials included in the treatment solution, or act as a preservative, but alcohols are not utilized for solubilizing the antifungal agent.

Suitable carrier fluids include water, glycerol, ethylene glycol, low molecular weight polyethylene glycol, the low molecular weight polyethylene glycol comprising an average molecular weight less than 1500, such as between 300 and 1500. In one embodiment, the carrier fluid comprises water. In one embodiment, the carrier fluid comprises water and glycerol. In one embodiment, the carrier fluid comprises water and ethylene glycol. In one embodiment, the carrier fluid comprises water and low molecular weight polyethylene glycol.

The treatment solution may also contain an antifungal agent solvent. A solvent is generally defined as a material that can dissolve other substances. In the treatment solution, the solvent keeps the other components of the solution in solution form, allowing the treatment solution to be wiped on the skin. Solvents may have a concentration of 0.01% to 40%, either individually or as a class. The class of materials that includes dioxolane is referred to generally as heterocyclic acetal solvent. Other ranges include 0.5% to 10%, 1% to 3%.

The antifungal agent solvent solubilizes the antifungal agent such that it is soluble in a carrier fluid that is essentially free of alcohols. The antifungal agent solvent is not intended to form an emulsion with the carrier fluid, but rather to be miscible with the carrier fluid and is stable. Being miscible means that the first fluid and the second fluid do not separate from each other, and being stable means that the separation does not occur even over time. It is further desired that the antifungal agent solvent is volatile and evaporates quickly after it is applied, it dries quickly, is non-greasy and non-oily.

A suitable antifungal agent solvent comprises a logKow between about −1 and about 1; or from about −1 to about 0. Kow (or log Kow) is the octanol/water partition coefficient and represents the ratio of a chemical's concentration in the octanol phase to its concentration in the aqueous phase of a two-phase octanol/water system. A negative or small Kow indicates an affinity for water miscibility or hydrophilicity. A log Kow between −1 and 1 means that the measures Kow is between $10^{-1}$ and 10, so the log Kow is −1 to 1.

$$Kow = \text{Concentration in octanol phase/Concentration in aqueous phase.}$$

A suitable antifungal agent solvent with a boiling point at 25° C., roughly room temperature, has a higher vapor pressure and would be considered to be volatile. Stated another way, a suitable antifungal agent solvent comprises a boiling point below 250° C., 200° C., below 180° C., 150° C., or below 100° C.

One embodiment of the treatment solution contains between about 0.01 wt % and about 10 wt % by weight of the treatment solution, such as between about 0.01 wt % and about 5 wt %, such as between about 0.5 wt % and about 3 wt %, such as 0.5 wt %, 1.0 wt %, 1.5 wt %, 2 wt %, 2.5 wt %, 3.0 wt %. The present formulation contains a weight ratio of the antifungal agent to the antifungal agent solvent from 1:6 to 6:1 inclusive, such as 1:1, 1:2, 1:3, 1:4, 1:5, 1:6 6:1, 5:1, 4:1, 3:1, 2:1, including any other amounts in the range.

| Antifungal Solvent | CAS No. | Structure | Boiling pt. ° C. | LogKow |
|---|---|---|---|---|
| 1,3-dioxolan; aka 1,4-dioxolane | 646-06-0 | 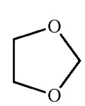 | 76.35 | −0.37 |
| 4-Methyl-1,3-dioxolane | 1072-47-5 | 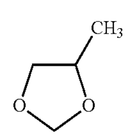 | 86 | 0.37920 |

| Antifungal Solvent | CAS No. | Structure | Boiling pt. ° C. | LogKow |
|---|---|---|---|---|
| 2-methyl-1,3-dioxolane | 497-26-7 | 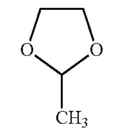 | 172-173 | |
| (2-Methyl-1,3-dioxolan-4-yl)methanol | 3773-93-1 | 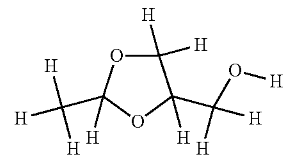 | 187.0 ± 0.0° C. | |
| 1,3-Dioxepane | 505-67-7 | 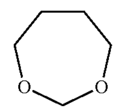 | 119 | 0.77090 |
| 1,3-Dioxolane-4-methanol | 5464-28-8 | 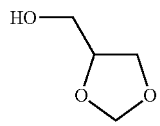 | 192-193° C. | |
| 5-Hydroxy-1,3-dioxane | 4740-78-7 | 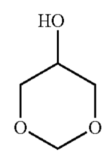 | 192-193° C. | −1.082 |
| Glycrol formal mixture (60:40) of 1,3-Dioxolane-4-methanol:5-Hydroxy-1,3-dioxane | 68442-91-1 | | 192-193° C. | |
| 1,4-dioxane | 123-91-1 | 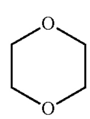 | 101.1 | |
| 1,3-dioxolane-2-one | 96-49-1 | 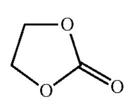 | 248 | |

A suitable antifungal agent solvent consists of an aprotic solvent with a log Kow between about −1 and about 1. A log Kow indicates that the solvent is soluble and miscible in water.

A suitable antifungal agent solvent may be selected from a heterocyclic acetyl solvent. A suitable antifungal agent solvent may be selected from 1,3-dioxolane, 4-Methyl-1,3-dioxolane, 2-methyl-1,3-dioxolane, (2-Methyl-1,3-dioxolan-4-yl) methanol, 1,3-Dioxepane, 1,3-Dioxolane-4-methanol, 5-Hydroxy-1,3-dioxane, Glycrol formal mixture (60:40) of 1,3-Dioxolane-4-methanol:5-Hydroxy-1,3-dioxane, 1,4-dioxane, 1,3-dioxolane-2-one, and mixtures thereof. Without being bound by a theory, the antifungal agent complexes with the antifungal solvent to form a water-soluble antifungal agent complex; the antifungal agent complex is miscible with the carrier. As such, an emulsion is not formed within the carrier fluid. In one embodiment, 1,3-dioxolane is the antifungal agent solvent. In one embodiment, 1,3-Dioxolane-4-methanol is the antifungal agent solvent. In one embodiment, 5-Hydroxy-1,3-dioxane is the antifungal agent solvent. These variations of dioxolane will be referred to generally as dioxolane in the current discussion.

As mentioned above, the treatment solution may contain several components, or it may be a carrier fluid having only the amount of antifungal needed. The US Food and Drug Administration requires that the antifungal ingredient have a set percentage of the solution by weight (wt %). In one embodiment, tolnaftate comprises 1 wt % of the solution, with a carrier fluid, such as water, or a mixture of water and glycerin (or other inactive ingredients) making up the remaining 99 wt %.

The treatment solution may also contain inactive ingredients, which will be discussed by each class of component, with given examples and ranges of concentration for each, with the understanding that the components themselves are optional beyond the active ingredient, as are any combination of ingredients. The active ingredient is the antifungal agent.

The term 'inactive ingredient' means an ingredient that is not antifungal, even though the ingredient may have other active properties, like conditioning, moisturizing, etc. The treatment solution may also contain inactive materials. The classes of materials used as inactive ingredients in the solution include emollients, surfactants, texture enhancers or texturizers, moisturizers, solvents, anti-inflammatory agents, deodorants, anti-bacterial, and curative ingredients. Curative ingredients improve texture, nourish the skin, reduce infections, increase circulation, etc.

For example, eucalyptus, peppermint and tea tree oil may be used as antibacterial ingredients but are not approved by the FDA as an antifungal for athlete's foot. The class of materials that include tolnaftate are generally referred to as naphthyl thionocarbamate actives.

As mentioned above, other active ingredients/antifungal agents could be used to treat athlete's foot, such as: clioquinol 3%; haloprogin 1%; miconazole nitrate 2%; povidone iodine 10%; undecylenic acid and its salts of calcium, copper and zinc, for a total undecylenate concentration of 10-25%; and clotrimazole. Other drugs previously mentioned, while not contained in the FDA's, may also be used as the antifungal agent.

It is important to note, all the drugs listed above are only approved by the FDA for the treatment of athlete's foot and the relief of symptoms due to athlete's foot. However, only tolnaftate is also approved for the prevention of athlete's foot.

Some embodiments of the treatment solution may include emollients. Emollients are generally defined as a preparation that softens or soothes the skin. These may moisturize to treat or prevent dry, rough, scaly, itchy skin and minor skin irritations. Emollient ingredients in the treatment solution may include glycerin, gossypium herbaceum (cotton seed oil), polyglyceryl-4 laurate, dilaurly citrate, ethylexyl stearate, and caprylyl glycol. These are just representative materials of emollients. These ingredients may have a range of concentration from 0.01% to 40%, either alone or as a class of ingredients. The emollient or combination of emollient may comprise from about 0.01 wt % to about 3 wt % by weight of the treatment solution. Suitable emollients may be selected from glycerin, gossypium herbaceum (cotton seed oil), polyglyceryl-4 laurate, dilaurly citrate, ethylexyl stearate, and caprylyl glycol (a combination of gossypium herbaceum(cotton seed oil), polyglyceryl-4 laurate, dilaurly citrate, ethylexyl stearate is sold under the tradename of TEGO WIPE LUX®). These ingredients may have a range of concentration from 0.01% to 40%, either alone or as a class of ingredients.

In addition to emollients, there may be moisturizers. Moisturizers may include glycerin, which can also act as an emollient, and tocopherol acetate, which is a form of vitamin E. Other forms of vitamin E may also be used. Vitamin E is a natural skin conditioning agent and antioxidant. Moisturizers may have a concentration of 0.01% to 40%, either individually or as a class. The present formulation of the treatment solution may optionally contain vitamin E, vitamin E esters, and salts thereof, such as tocopheryl acetate, tocopheryl succinate, tocopheryl nicotinate, tocopheryl linolate, alpha-tocopheryl phosphates. Suitable levels of vitamin E, vitamin E esters and salts thereof is from about 0.001 to about 0.5 wt % by weight of the treatment solution. In one embodiment tocopheryl acetate is present at about 0.01 wt %.

These and other embodiments may include another class of materials consisting of surfactants. A surfactant is a material that alters the surface energy of a substance, most commonly it tends to reduce the surface tension of a liquid in which it dissolved. In cleaning applications, it tends to reduce the adherence of particles to surfaces to allow them to be lifted away. Examples include sodium lauroyl sarcosinate, a foaming and cleansing agent made form coconut oil. Another example consists of sodium laurylamphoacetate, another foaming and cleansing agent that also conditions the skin. Yet another example consists of sorbitan laurate, it helps water mix with dirt and oil to allow the water to carry them away. Surfactants may have a concentration of 0.01% to 40%, either individually or as a class.

The use of surfactants is not intended to create an emulsion of the antifungal agent in the carrier solution, as discussed above. Rather, the amounts of surfactant should be such that a foaming or cleaning of soils from the skin surface contacting by the treatment is accomplished. In one embodiment, surfactants are selected from sodium lauroyl sarcosiate and sodium laurylamphoacette, and are present between about 0.01% to about 10 wt % by weight of the treatment solution, such as from about 0.1 wt % to about 1.5 wt % individually and together less than 3 wt % by weight of the treatment solution.

Embodiments of the treatment solution may optionally contain a thickening agent between about 0.01 wt % to about 10 wt % by weight of the treatment solution. The thickening agent may be present from about 0.01 wt % to about 3 wt % by weight of the treatment solution. A suitable thickening agent may be selected from ammonium acryloyldimethyltaurate/Vp copolymer, sodium polyacrylate, a mixture of caprylic/capric triglyceride and ammonium acryloyldimethyltaurate/VP copolymer, xanthan gum, karaya gum, alginates, sclerotium gum, galactoarabinan, diutan gum, guar gum, locust bean gum, and gellan gum; fumed silicas and treated silicas; silicates; starch and its hydrophilic derivatives; and mixtures thereof. In one embodiment the inactive ingredients include ammonium acryloyldimethyltaurate/Vp copolymer. It can act as a texture enhancer, it thickens the foam and makes it smooth against the skin. Texture enhancers may have a concentration of 0.01% to 40%, either individually or as a class.

Other inactive ingredients may include alpha hydroxy acid and/or other exfoliants, vitamin C, vitamin B, vitamin K, and various essential oils, such as, without limitation, tea tree oil, coconut oil, lanolin, citric acid, aloe vera, lavender, saline, mineral oil, argan oil, avocado oil, jojoba oil, peppermint oil, eucalyptus oil, etc.

One or more essential oil(s) may be present from about 0.001 wt % to 1 wt % of the treatment solution, such as from about 0.01 wt % to about 0.5 wt % of the treatment solution. Suitable essential oils may be selected to provide a conditioning or skin benefit. Suitable essential oils may be selected from chamomile oil, geranium oil, peppermint oil, eucalyptus oil, juniper oil, sandalwood oil, rose oil, lavender oil, and mixtures thereof.

Two essential oils that have beneficial and therapeutic effects are eucalyptus and peppermint. Eucalyptus has anti-inflammatory, deodorizing, antiseptic, antibacterial and stimulating properties that may make the skin on the user's foot or feet feel better. Similarly, peppermint has nourishing, texture-improving, infection-reducing, circulation-increasing properties and blends well with eucalyptus. When these two inactive ingredients are initially applied to the surface of the skin, the skin feels cool and fresh without the negative side effects of alcohol. These ingredients may have a concentration in the range from 0.01 wt % to 5% each, such as 0.2 wt %.

In one embodiment, tolnaftate comprises 1 wt % of the solution, peppermint comprises 0.25 wt %, eucalyptus comprises 0.25 wt % relative to the solution, with any combination of the other inactive ingredients making up the 98.5 wt %. Other embodiments have peppermint and eucalyptus at 0.1 wt % each. Still other embodiments have peppermint and eucalyptus at 1.0 wt % each.

In one embodiment, tolnaftate comprises 1 wt % of the solution, peppermint has a concentration range of 0.01 wt % to 5 wt % relative to the solution, and eucalyptus has a concentration in the range of 0.01 wt % to 5 wt % relative to the solution, with any combination of the other inactive ingredients making up a range of 89 wt %-98.98 wt % relative to the solution.

One should note that the oils used here do not interact with the antifungal agent or antifungal agent solvent. The antifungal agent, such as tolnaftate, does not dissolve in, nor does it become solubilized in the oils. One current solution consists of dissolving tolnaftate into jojoba oil, and does not use water or glycol. The antifungal agent in the embodiments here are solubilized by the antifungal agent solvent.

One ingredient that will not be included in the treatment solution is alcohol. Alcohol is often used in skincare or makeup products. It gives the products a quick-drying finish, immediately degreases the skin, and feels weightless on the skin, so it often appeals to users, especially those with oily skin. Typically, the alcohol used is listed as SD alcohol, denatured alcohol, isopropyl alcohol, or ethanol. Denatured alcohol is a drying type of alcohol that aggravates and weakens the skin. However, the use of alcohol will aggravate and be cruel to the skin. Consequences include dryness, erosion of the skin surface, and strain on skin replenishment, renewal, and rejuvenation. The FDA discourages the use of alcohol for bodily cleansing. Ethanol also destroys skin cells, called apoptosis. Alcohol, when applied to any skin that is broken or cut, will cause burning pain in conditions such as athlete's foot. For feet, which often have blisters and sore spots, the use of alcohol seems ill-advised, although the anti-bacterial properties are well-know.

Using dioxolane as a solvent, combined with a surfactant and water, allows the active ingredient to be completely solubilized and stable, meaning the active ingredient is completely in solution form and remains that way, without the use of alcohol. "Without the use of alcohol" as used here is equivalent to "alcohol-free" or "essentially free of alcohol" and means that the solution contains between zero (0 wt %) and 1 wt % alcohol. This means that alcohol is not intentionally added to the solution.

The University of Toronto's departments of Clinical Pharmacology, Dermatology and Medicine conducted a dermatological study that illustrated the correlation of ethanol exposure and skin cell destruction. Application of 3% ethanol to skin cells over the course of two days resulted in an increase of cell death by 26%. Most antiseptic wipes contain 60% alcohol, more than 20 times the amount tested in the study. The study also revealed that alcohol terminates the substances in skin cells that reduce inflammation and defend against free radicals.

According to the Journal of Occupational Medicine and Toxicology, Alcohol (Ethanol) is a topical penetration enhancer. Ethanol enters the skin and removes significant quantities of the lipid barrier material from the stratum corneum. The barrier function of the skin relies almost entirely on the stratum corneum. By extracting the lipids, the skin barrier function weakens and may render the membrane more permeable.

The stratum corneum acts as the first line of defense against the external environment. It is a compact layer of cells and lipids that has two critical functions: it protects our bodies from bacteria, UV damage and other assaults; and prevents natural moisture from escaping, to keep skin hydrated. Most, if not all, currently available over-the-counter treatment products for athlete's foot use alcohol.

However, if one were to add alcohol, the mixture would remain 'low alcohol' defined here as having 6 wt % or less of the final solution. The solution could contain one of 5 wt %, 4 wt %, 3 wt %, 2 wt %, or 1 wt %. That percentage would result from an arithmetic sum of the individual levels of all alcohols. In one embodiment, the alcohols could be selected from the group consisting of SD ethanol, denatured ethanol, and isopropyl alcohol, but no limitation to the types of alcohols is intended. Other ranges of low-alcohol solutions may have 5% or less, or 2% or less.

Some embodiments relate to an antifungal and conditioning wipe article comprising a substrate treatment solution having an antifungal agent, an antifungal agent solvent, and a carrier fluid. The solution may be delivered through a wipe to a person's feet, or other body part suffering from a fungal infection, or take the form of a cream, lotion, or fluid. The treatment solution will treat and prevent such fungal conditions as athlete's foot, and provides healing and soothing properties. It eliminates odors, and has both a fresh scent and leaves a user's body parts smelling fresh. As discussed above, the treatment solution should be essentially free of alcohols.

As used here, the terms "substrate" and "wipe" refer to a piece or complete item of material that can accept the treatment solution. The wipe, or substrate, could take one of many forms, including creped or un-creped tissue, coform products, hydroentangled (spun lace) webs, air-laid mats, fluff pulp, nonwoven webs, woven webs, and composites of any of the above.

FIG. 1 shows an embodiment of a wipe or substrate 10. The surface of the wipe or substrate may have a quilted surface 12. As discussed below, the wipe may have texture in the form of bumps, such as those shown in the region 14. The texture may cover the entire wipe or just a portion of it. The texture may contribute to the exfoliation of the user's feet, not just treating the skin by applying the solution, but also by loosening and then removing infected dead skin cells.

In one embodiment, the substrate may take the form of lyocell. A common, commercially available form of lyocell is sold under the name Tencel®. Lyocell typically consists of wood-based cellulose fibers made from wood pulp. It is a form of rayon, not to be confused with viscose rayon.

The US Federal Trade Commission defines lyocell as a fiber "composed of cellulose precipitated from an organic solution in which no substitution of the hydroxyl groups takes place and no chemical intermediates are found." It is classified as a sub-category of rayon. lyocell can be blended with many different fibers, including silk, cotton, rayon, polyester, linen, nylon, and wool. One blend of lyocell, under the trademark Tencel+Plus™ is lyocell from eucalyptus. This fits well with the treatment solution, as some embodiments of the treatment solution uses eucalyptus.

Regardless of the material used, the substrate should resist dissolving in the treatment solution when stored as an antifungal and conditioning wipe article. Some of this may be determined by the basis weight of the wipe article. The basis weight is the weight per unit area of the substrate or wipe, and is often measured by weighing a sample of know size and determining the grams of weight per square meter (m²). The substrate sheet of use in some embodiments may have a basis weight ranging from about 25 g/m² to about 75 g/m², such as a basis weight ranging from about 40 g/m² to about 60 g/m². In one embodiment, the substrate has a weight of 50 grams per square meter, but any weight that is sufficient to avoid rolling up during use will work. Other possibilities include ranges of 25 to 75 grams per square meter, or 40 to 60 grams per square meter. One embodiment has a weight of 50 grams per square meter.

Figure 2:
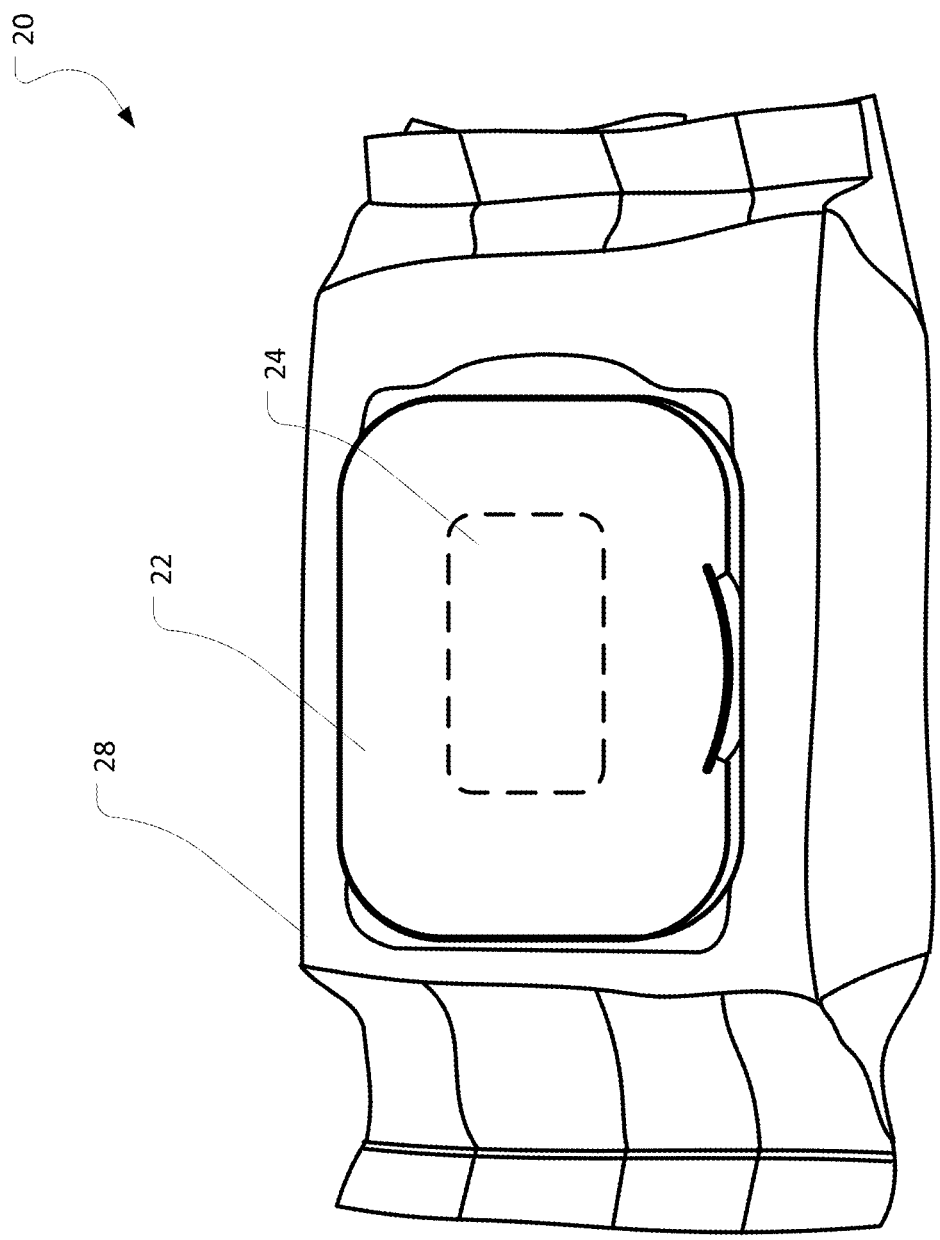
FIG. 2 shows an embodiment of a pop-up package for antifungal wipes.
Figure 3:
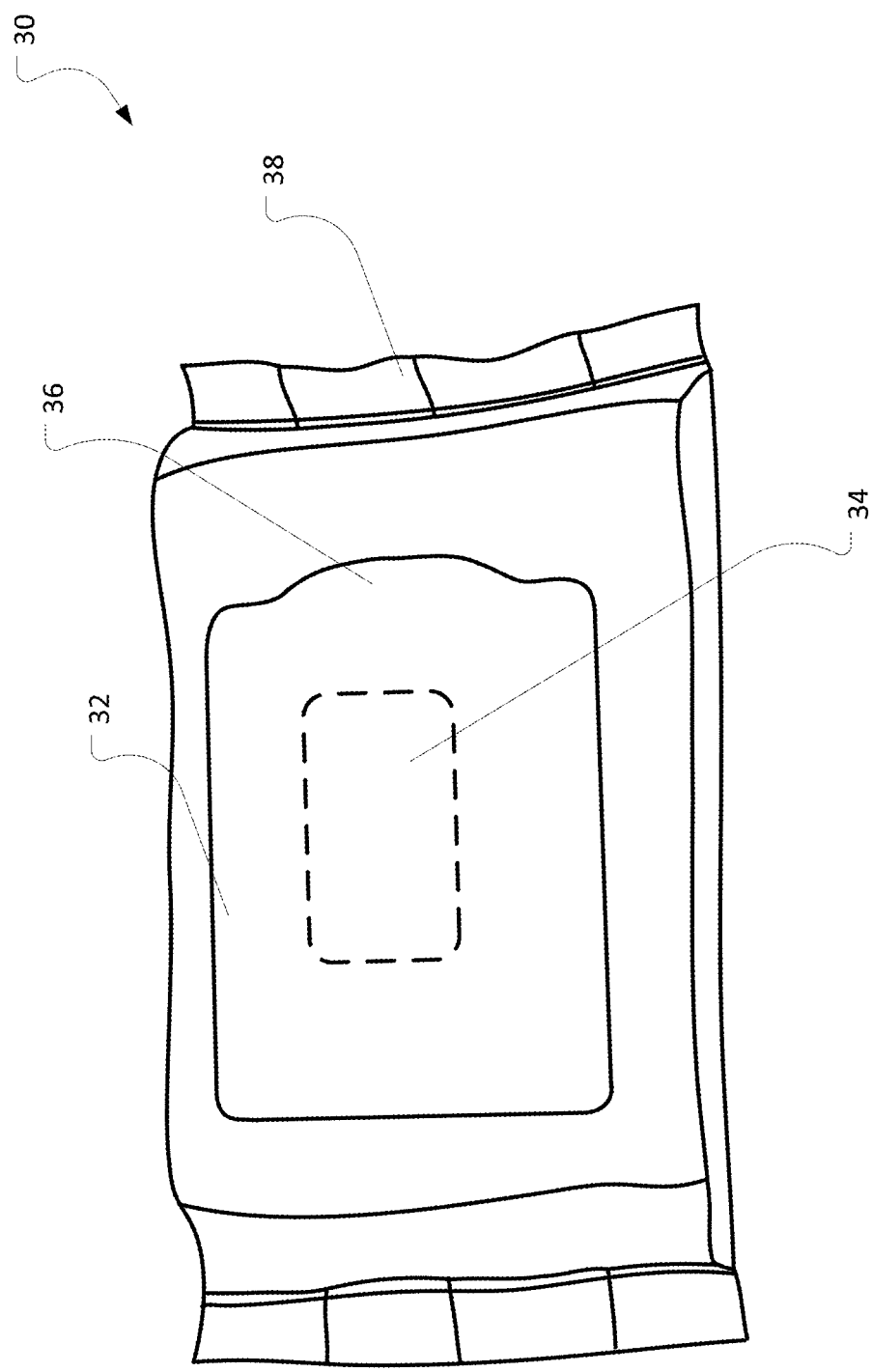
FIG. 3 shows an embodiment of a flat package for antifungal wipes.
Figure 4:
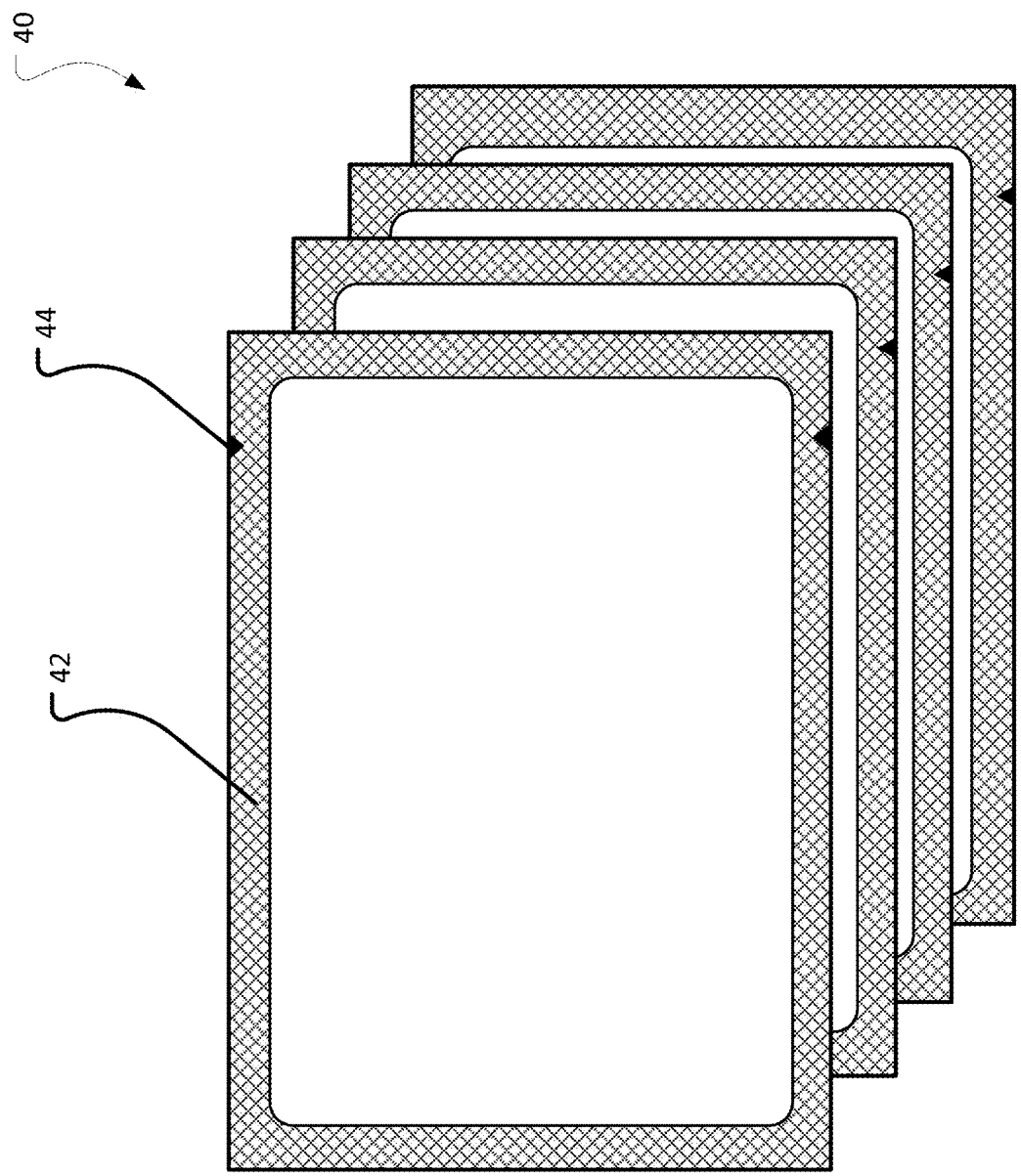
FIG. 4 shows an embodiment of individual packages for antifungal wipes.

The wipes may be stored in a container, such as a pop-up container shown in FIG. 2, similar to those used for facial tissue or baby wipes, in a flat pack such as those shown in FIG. 3, where the user has to open and extract the wipe, or in individual packets. As shown in FIG. 2, the container 20 may consist of a lid 22 and a body 28. A stack of wipes, not visible, are accessed through an opening 24, through which the wipe can be pulled. A flat pack 30, such as that shown in FIG. 3, typically has a body 38. The wipes reside inside the pack. A user would pull the flap 32 away from the body 38, which may be held close by some sort of a closure 36. The flap 32 covers the opening 34. Closure 36 may comprise some sort of adhesive or sticky patch, electrostatic cling, as examples of closures that can keep the flap tight enough to the body to avoid the solution leaking or evaporating, which would in turn cause the wipes to dry. Alternative packages may include individually wrapped single packets as shown in FIG. 4. The individual packages 40 have a sealed body 42 and may have a notch 42 to allow a user a convenient way to open the package.

These are just some examples and are in no way intended to limit the scope of any embodiments to a particular container. The treatment solution is applied to the wipe and then packaged and stored, so resisting dissolving allows for longer storage.

The wipe is used to deliver the solution to the affected surface or to just be applied to the foot for preventative, healing, or soothing reasons. The user will be wiping or scrubbing the surfaces of the feet, including the top, bottom, sides and on top of and between the toes, or other affected body parts. The wipe should have sufficient structural integrity that it does not roll up, rip, or otherwise fall apart when the user wipes the foot with them.

The substrate may be smooth, without texture, and have a thickness in the range of 0.40 millimeter (mm), or it may also have a light texture for comfort and/or exfoliation. In one embodiment, the texture consists of bumps or dots that form a pattern on the surface of the wipe, and the dots have a height above the surface of the wipe in the range of 0.1 to 500 microns, such as from 50 to 100 microns, or from 50 to 80 microns, more specifically from 55 to 75 microns. One embodiment has dots having a thickness of 70 microns. The texture may result from adding material to the wipe substrate by printing or spraying a material that is either solid or cures after application, or deforming or heating the wipe such as by passing the wipe through a roller nip, or by calendaring.

If a specific height range for the texture is desired, the surface texture of a wipe may be measured using an optical 3D measuring device also known as MikroCAD Optical Profilometer by GFM™ (GFMesstechnik GmbH, Germany). The measuring device utilizes a CCD (Charged Coupled Device) camera coupled with a stripe light projector (SLP) where the object to be measured is angular lighted under a defined angle (45°) with an array of equidistant stripes. Thus, height information is included in stripe position as well as the grey value providing high resolution of surface geometries. Image analysis software provided by GFM™ (ODSCAD 5.075 E) is utilized for characterizing texture (heights) on a textured nonwoven material sample. Test samples of a wipe are cut to 18 cm length in the MD and 10 cm length in the wipes' CD. For these samples the MikroCAD optical profilometer from GFMesstechnik GmbH is used to measuring texture (height) for the samples. The measurement is performed on both sides of the samples in a relaxed state without any strain and after about 25% strain in the CD. All the images are scaled and calibrated before measuring the actual heights in micrometers (µm). A dot is marked on each of samples to enable a repeatable positioning of the instrument from side to side.

According to the *Handbook of Non-Prescription Drugs* (2017), rubbing a solution into an affected area has a higher efficacy than spraying the solution onto the area. Only by rubbing the solution into the area with a textured wipe will achieve a higher efficacy while exfoliating to remove infected dead skin cells. In the embodiments where the solution is contained in a cream, lotion or fluid form, the user would be directed to use a towel, piece of other material, cloth or paper towel to rub the solution into the skin.

The substrate receives the treatment solution to a saturation level that will allow the treatment solution to be applied to the user's foot or feet, while at the same time not being too drippy or messy. "Saturation loading" and "lotion loading" are used interchangeably herein and refer to the amount of liquid composition applied to the wipe. In general, the amount of liquid composition applied may be chosen in order to provide maximum benefits to the end product comprised by the wipe. Saturation loading is typically expressed as grams of liquid composition per gram of dry wipe. In one embodiment, the substrate is loaded to range of 300 to 400%.

In this manner, an antifungal treatment solution with several other beneficial properties is applied to a substrate to a saturation level that it will allow the solution to be usefully applied to the surfaces of a user's foot or feet. The solution will treat and prevent such fungal conditions as athlete's foot, as well as providing healing and soothing properties. It eliminates odors, and both has a fresh scent and leaves a user's feet smelling fresh.

While the embodiments above refer to the application of the solution through a wipe to the user's feet, the solution may be applied by a cream, lotion or other fluid to other parts of the user's skin than the feet. It can be used to fight many different types of fungal infections, including jock itch, athlete's foot, ringworm, while not being limited to those examples. This includes the application by an aerosol spray, by inclusion of an aerosol propellant in the solution and putting the solution in an aerosol container, and includes a pump sprayer, that typically uses air in a pump spray container. However, as noted above, wiping the feet with the solution provides beneficial effects.

Emnbodiments

One embodiment of the treatment solution disclosed comprises an effective amount of an antifungal agent, an antifungal agent solvent, and a carrier fluid where the antifungal agent is selected from a naphthyl thiocarbamate, the antifungal agent solvent is selected from a heterocyclic acetyl solvent and the carrier fluid is essentially free of alcohols. The treatment solution as described above formulated where the carrier fluid comprises water, glycerol, ethylene glycol, low molecular weight polyethylene glycol and mixtures thereof. An embodiment of the treatment solution as described above formulated where the carrier fluid comprises water and glycerol. An embodiment of the treatment solution as described above formulated where the carrier fluid is water. Additional embodiments of the treatment solution as described above are formulated where the carrier fluid is water an low molecular weight polyethylene glycol, the low molecular weight polyethylene glycol comprising an average weight average molecular weight less than 1500, such as between 300 and 1500.

Embodiments of the present treatment solution comprising an effective amount of an antifungal agent, an antifungal agent solvent, and a carrier fluid where the carrier fluid is essentially free of alcohol and the antifungal agent solvent is essentially free of alcohol.

Embodiments of the present treatment solution comprising an effective amount of an antifungal agent; an antifungal agent solvent with a logKow between about −1 and about 1; or from about −1 to about 0; and water; where the treatment solution is essentially free of alcohol. Embodiments of the treatment solution as described above wherein the antifungal agent solvent comprises a boiling point below 150° C., or below 100° C. to about 30° C. The treatment solution as described above wherein the ratio of the antifungal agent to the antifungal agent solvent is from 1:6 to 6:1, such as 1:1, 1:2, 1:3, 1:4, 1:5, 1:6, 6:1, 5:1, 4:1, 3:1, and 2:1 including any ratio within.

Embodiments of the present treatment solution as described above wherein the antifungal agent solvent is selected from a heterocyclic acetyl solvent. In one embodiment, the antifungal agent solvent is selected from 1,3-dioxolan, 4-Methyl-1,3-dioxolane, 2-methyl-1,3-dioxolane, (2-Methyl-1,3-dioxolan-4-yOmethanol, 1,3-Dioxepane, 1,3-Dioxolane-4-methanol, 5-Hydroxy-1,3-dioxane, Glycrol formal mixture (60:40) of 1,3-Dioxolane-4-methanol:5-Hydroxy-1,3-dioxane, 1,4-dioxane, 1,3-dioxolane-2-one, and mixtures thereof.

In one embodiment, the treatment solution as described above where the antifungal agent is selected from tolnaftate, clioquinol, haloprogin, miconazole nitrate, povidone iodine, undecylenic acid and its salts, clotrimazole and mixtures thereof, and terbinafine hydrochloride. The treatment solution as described above where the antifungal agent is tolnaftate at a concentration of approximately 1%.

Other embodiments may use medications not included in the FDA's monograph, including ketoconazole, an imidazole, (1-[4-(4-{[(2R,4S)-2-(2,4-Dichlorophenyl)-2-(1H-imidazol-1-ylmethyl)-1,3-dioxolan-4-yl]methoxy}phenyl)-1-piperazinyl]ethanone); sulconazole, an imidazole (1-{2-[(4-Chlorobenzyl)sulfanyl]-2-(2,4-dichlorophenyl)ethyl}-1H-imidazole); sertaconazole, an imidazole (1-{2-[(7-Chloro-1-benzothiophen-3-yl)methoxy]-2-(2,4-dichlorophenyl) ethyl}-1H-imidazole); betamethasone ((11β,16β)-9-Fluoro-11,17,21-trihydroxy-16-methylpregna-1,4-diene-3,20-dione)+clotrimazole, an imidazole (1-[(2-Chlorophenyl)(diphenyl)methyl]-1H-imidazole); ciclopirox (6-Cyclohexyl-1-hydroxy-4-methyl-2(1H)-pyridinone); econazole (1-{2-[(4-Chlorobenzyl)oxy]-2-(2,4-dichlorophenyl)ethyl}-1H-imidazole); naftifin ((2E)-N-Methyl-N-(1-naphthylmethyl)-3-phenyl-2-propen-1-amine); oxiconazole ((1Z)-N-[(2,4-Dichlorobenzyl)oxy]-1-(2,4-dichlorophenyl)-2-(1H-imidazol-1-yl)ethanimine); butenafine, a Trimethyl-amine, (N-Methyl-1-[4-(2-methyl-2-propanyl)phenyl]-N-(1-naphthylmethyl)methanamine); undecylenic acid+cholorozylenol (para-chloro-meta-xylenol).

Embodiments of the treatment solution as described above which additionally comprise essential oils. Some embodiments of the treatment solution as described above where the essential oils are selected from chamomile oil, geranium oil, peppermint oil, eucalyptus oil, juniper oil, sandalwood oil, rose oil, lavender oil, and mixtures thereof.

Embodiments of the treatment solution as described above which further comprise vitamin E and vitamin E esters, and salts thereof, such as tocopheryl acetate and tocopheryl succinate, tocopheryl nicotinate, tocopheryl linolate, alpha-tocopheryl phosphates.

Embodiments of the treatment solution as described above which further comprise between about 0.01% to about 10% of one or more surfactants. These embodiments may contain one or more surfactants selected from lauroyl sarcosinate, lauryl amphoacetate, sorbitan laurate, their salts and mixtures thereof. Other embodiments may comprise the one or more surfactants selected from sodium lauroyl sarconsiate and sodium lauryl amphoacetate; the treatment solution comprises between about 0.01% to about 10 wt % of the one or more surfactants.

Embodiments of the present treatment solution described above further comprise an emollient. Embodiments or these treatment solutions described where the emollient comprises glycerin, gossypium herbaceum (cotton seed oil), polyglyceryl-4 laurate, dilauryl citrate, ethylhexyl stearate, caprylyl glycol and mixtures thereof.

Embodiments of the present treatment solution described above further comprise a thickening agent. The embodiments of treatment solution described above where the thickening agent is selected from ammonium acryloyldimethyltaurate/Vp copolymer, sodium polyacrylate, a mixture of caprylic/capric triglyceride and ammonium acryloyldimethyltaurate/VP copolymer, xanthan gum, karaya gum, alginates, sclerotium gum, galactoarabinan, diutan gum, guar gum, locust bean gum, and gellan gum; fumed silicas and treated silicas; silicates; starch and its hydrophilic derivatives; and mixtures thereof.

Embodiments of the treatment solution as described above wherein the antifungal agent is not water soluble; the antifungal agent complexes with the antifungal solvent to form a water-miscible antifungal agent complex; the antifungal agent complex is miscible with the carrier fluid.

Embodiments of the present treatment solution comprising an effective amount of an antifungal agent, the antifungal agent is solubilized in an antifungal agent solvent, the antifungal agent solvent is miscible in water; wherein the treatment solution is essentially free of alcohols.

Embodiments of the present treatment solution as described above wherein the antifungal agent solvent is selected from 1,3-dioxolan, 4-Methyl-1,3-dioxolane, 2-methyl-1,3-dioxolane, (2-Methyl-1,3-dioxolan-4-yO-methanol, 1,3-Dioxepane, 1,3-Dioxolane-4-methanol, 5-Hydroxy-1,3-dioxane, Glycrol formal mixture (60:40) of 1,3-Dioxolane-4-methanol:5-Hydroxy-1,3-dioxane, 1,4-dioxane, 1,3-dioxolane-2-one, and mixtures thereof. Some of the embodiments described above where the antifungal agent is selected from tolnaftate, clioquinol 3%; haloprogin 1%; miconazole nitrate 2%; povidone iodine 10%; undecylenic acid and its salts 10-25%; clotrimazole 1%; terbinafine hydrochloride; and mixtures thereof.

Embodiments of the antifungal and conditioning wipe article comprise a substrate, and a treatment solution comprising an effective amount of an antifungal agent, an antifungal agent solvent and a carrier fluid. Embodiments of the antifungal and conditioning wipe article as described above where the substrate is insoluble in the treatment solution. Some of the embodiments of the wipe article described above where the substrate is woven or non-woven sheet comprising wood based fibers composed of cellulose precipitated from an organic solution in which no substitution of fiber hydroxyl group takes place (lyocell). Other embodiments of the wipe articles described above where the substrate sheet also comprises fibers of the group consisting of silk fibers cotton fibers rayon fibers polyester linen fibers nylon fibers wood fibers and mixtures thereof. Some embodiments of the wipe articles described above wherein the substrate has a basis weight ranging from about 25 g/m² to about 75 g/m². Other embodiments of the wipe articles described above wherein the substrate has a basis weight ranging from about 40 g/m² to about 60 g/m². Wipe articles described above where the substrate is textured having a profilometric range of 0.01 microns to 500 microns.

A packaged article comprises a plurality of antifungal and conditioning wipes as described above and a container. The package article as described above wherein the container is selected from the group consisting of a pop-up container a flat-pack or, tub, a refill package, resealable bag, or a single, individually packaged wipe.

In this manner, an antifungal treatment solution with several other beneficial properties is applied to a substrate to a saturation level that it will allow the solution to be usefully applied to the surfaces of a user's skin at the tinea infection affected area, such as a foot or feet. The solution will treat and/or prevent such fungal conditions, such as athlete's foot, as well as providing healing and soothing properties. It eliminates odors, and both has a fresh scent and leaves a user's feet smelling fresh.

One example of an embodiment of the alcohol free antifungal treatment solution is made having the following formulation.

| Component | Amount (wt %) |
| --- | --- |
| Glycerine | 0.25%-0.50% |
| Dioxolane | 1.00%-4.00% |
| Tolnaftate | At least 1.00% |
| Sodium Lauroyl Sarcosinate | 1.00%-1.50% |
| Sodium Lauroamphoacetate | 0.75%-1.25% |
| Mentha Piperita Oil (Peppermint Oil) | 0.075%-0.125% |
| Eucalyptus Gloulus Leaf Oil (Eucalyptus Oil) | 0.075%-0.125% |
| Blend: Ethylhexyl Stearate, Sorbitan Laurate, Phenoxyethanol, Gossypium Herbaceum (Cotton) Seed Oil, Polyglyceryl-4 Lautate, Dilauryl Citrate (TEGO Wipe Lux, Evonik) | 0.5%-1.50% |
| Blend: Phenoxyethanol and Caprylyl Glycol | 0.25%-0.075% |
| Tocopheryl Acetate (Vitamin E) | 0.005%-0.0125 |
| Ammonium Acryloyldimethyltaurate/VP Copolymer | 0.05%-1.25% |
| Water | q.s. to 100% |

EXAMPLE 2

| INCI Name | Trade Name | Supplier | % |
| --- | --- | --- | --- |
| Water | DI Water | Manufacturer | 91.69% |
| Glycerin | Glycerin Vegetable, USP | Choice | 0.35% |
| Dioxolane | Dioxolane Ultra Pur | BASF | 2.00% |
| Tolnaftate | Tolnaftate | Choice | 1.00% |
| SodiumLauroyl Sarcosinate | Sensactive L-30 | Chemyunion | 1.25% |
| Sodium Lauroamphoacetate | Pureact LAA | Innospec | 1.00% |
| Mentha Piperita Oil | Peppermint Oil | Jedwards International, Inc. | 0.10% |
| Eucalyptus Globulus Leaf Oil | Biochemica ® Eucalyptus Oil | Hallstar | 0.10% |
| Ethylhexyl Stearate, Sorbitan Laurate, Phenoxyethanol, Gossypium Herbaceum (Cotton) Seed Oil, Polyglyceryl-4 Laurate, Dilauryl Citrate | TEGO Wipe Lux | Evonik | 1.00% |
| Phenoxyethanol (and) Caprylyl Glycol | Symocide PC | Symrise | 0.50% |
| Tocopheryl Acetate | Vitamin E Acetate | Choice | 0.01% |
| Ammonium Acryloyldimethyltaurate/VP Copolymer | Aristoflex AVC | Clariant—Personal Care | 1.00% |
| | | Total | 100.00% |

EXAMPLE 3

| INCI Name | Trade Name | Supplier | % |
| --- | --- | --- | --- |
| Water | DI Water | Manufacturer | q.s. |
| Propanediol | Zemea | Dupont, Tate and Lyle | 5.00% |
| Disodium EDTA | Disodium EDTA | Choice | 0.10% |
| Dioxolane | Dioxolane Ultra Pur | BASF | 3.00% |
| Tolnaftate | Tolnaftate | Choice | 1.00% |
| Sodium Lauroyl Sarcosinate | Sensactive L-30 | Chemyunion | 1.50% |
| Sodium Lauroamphoacetate | Pureact LAA | Innospec | 1.25% |
| Mentha Piperita Oil | Peppermint Oil | Jedwards International, Inc. | 0.10% |
| Eucalyptus Globulus Leaf Oil | Biochemica ® Eucalyptus Oil | Hallstar | 0.10% |
| Ethylhexyl Stearate, Sorbitan Laurate, Phenoxyethanol, Gossypium Herbaceum (Cotton) Seed Oil, Polyglyceryl-4 Laurate, Dilauryl Citrate | TEGO Wipe Lux | Evonik | 1.00% |
| Phenoxy ethanol (and) Caprylyl Glycol | Symocide PC | Symrise | 0.50% |
| Tocopheryl Acetate | Vitamin E Acetate | Choice | 0.01% |
| Ammonium Acryloyldimethyltaurate/VP Copolymer | Aristoflex AVC | Clariant—Personal Care | 1.00% |
| | | Total | 100.00% |

Example 4 consists of any of the above examples, with the antifungal agent replaced with terbinafine hydrochloride in the range of 1.0 to 3.0 wt %, with adjustments made to at least one of the ranges of the dioxolane or water.

Example 5 consists of any of the above examples, with the antifungal agent replaced with butenafine hydrochloride in the range of 1.0 to 3.0 wt %, with adjustments made to at least one of the ranges of the dioxolane or water.

Example 6 consists of any of the above examples, with the antifungal agent replaced with clotrimazole in the range of 1.0 to 3.0 wt % with adjustments made to at least one of the ranges of dioxolane or water.

Example 7 consists of any of the above examples, with the antifungal agent replaced with clioquinol in the range of 1.0 to 3.0 wt % with adjustments made to at least one of the ranges of dioxolane or water.

Example 8 consists of any of the above examples, with the antifungal agent replaced with haloprogin in the range of 1.0 to 3.0 wt % with adjustments made to at least one of the ranges of dioxolane or water.

Example 9 consists of any of the above examples, with the antifungal agent replaced with miconazole nitrate in the range of 1.0 to 3.0 wt % with adjustments made to at least one of the ranges of dioxolane or water.

Example 10 consists of any of the above examples with the antifungal agent replace with povidone iodine in the range of 1 wt %-12 wt %, with adjustments made to at least one of the ranges of dioxolane or water.

Example 11 consists of any of the above examples with the antifungal agents replaced with undecylenic acid in the range of 10 wt % to 25 wt %, with adjustments made to at least one of the ranges of the dioxolane or water.

Example 12 consists of any of the above examples with the antifungal agents replaced with one of: ketoconazole, an imidazole, (1-[4-(4-{[(2R,4S)-2-(2,4-Dichlorophenyl)-2-(1H-imidazol-1-ylmethyl)-1,3-dioxolan-4-yl]methoxy}phenyl)-1-piperazinyl]ethanone); sulconazole, an imidazole (1-{2-[(4-Chlorobenzyl)sulfanyl]-2-(2,4-dichlorophenyl)ethyl}-1H-imidazole); sertaconazole, an imidazole (1-{2-[(7-Chloro-1-benzothiophen-3-yl)methoxy]-2-(2,4-dichlorophenyl)ethyl}-1H-imidazole); betamethasone ((11β,16β)-9-Fluoro-11,17,21-trihydroxy-16-methylpregna-1,4-diene-3,20-dione)+clotrimazole, an imidazole (1-[(2-Chlorophenyl)(diphenyl)methyl]-1H-imidazole); ciclopirox (6-Cyclohexyl-1-hydroxy-4-methyl-2(1H)-pyridinone); econazole (1-{2-[(4-Chlorobenzyl)oxy]-2-(2,4-dichlorophenyl)ethyl}-1H-imidazole); naftifin ((2E)-N-Methyl-N-(1-naphthylmethyl)-3-phenyl-2-propen-1-amine); oxiconazole ((1Z)-N-[(2,4-Dichlorobenzyl)oxy]-1-(2,4-dichlorophenyl)-2-(1H-imidazol-1-yl)ethanimine); butenafine, a Trimethylamine, (N-Methyl-1-[4-(2-methyl-2-propanyl)phenyl]-N-(1-naphthylmethyl)methanamine); undecylenic acid+ cholorozylenol (para-chloro-meta-xylenol) in the range of 1.0 wt % to 15 wt %, with adjustments made to at least one of the ranges of the dioxolane or water.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by below claims.

What is claimed is:

1. A wipe, comprising:
a substrate; and
a treatment solution impregnated into the substrate, the treatment solution comprising:
an antifungal agent comprising a naphtyl thiocarbamate;
a carrier fluid; and
an antifungal agent solvent comprising a dioxolane solvent miscible with the carrier and having a logKow with a range of −1 to 1, the dioxolane comprising one selected from the group selected from: 1,3-dioxolane, 4-Methyl-1,3-dioxolane, 2-methyl-1,3-dioxolane, (2-Methyl-1,3-dioxolane-4-yl) methanol, 1,3-Dioxepane, 1,3-Dioxolane-4-methanol, 5-Hydroxy-1,3-dioxane, Glycrol formal mixture (60:40) of 1,3-Dioxolane-4-methanol: 5-Hydroxy-1,3-dioxane, 1,4-dioxane, 1,3-dioxolane-2-one, and mixtures thereof;
wherein the treatment solution has an alcohol content of 6 wt % or below of the total solution.

2. The wipe as claimed in claim 1, wherein the treatment solution has an alcohol content of 5 wt % or below.

3. The treatment solution as claimed in claim 1, wherein the treatment solution has an alcohol content of 4 wt % or below.

4. The treatment solution as claimed in claim 1, wherein the treatment solution has an alcohol content of 3 wt % or below.

5. The treatment solution as claimed in claim 1, wherein the treatment solution has an alcohol content of 2 wt % or below.

6. The wipe as claimed in claim 1, wherein the antifungal agent comprises tolnaftate.

7. The wipe as claimed in claim 1, wherein the substrate comprises at least one selected from the group consisting of: creped tissue; un-creped tissue; coform products; hydroentangled webs; air-laid mats; fluff pulp; nonwoven webs; woven webs; composites of any of the previous; lyocell; viscose rayon; blends of lyocell; and blends of viscose rayon.

8. The wipe claimed in claim 1, wherein the substrate has a basis weight in the range of 40 to 60 grams per square meter.

9. A wipe, comprising:
a substrate; and
a treatment solution impregnated into the substrate, the treatment solution comprising:
an antifungal agent comprising a naphthyl thiocarbamate;
a carrier fluid; and
an antifungal agent solvent comprising a dioxolane solvent miscible with the carrier and having a logKow with a range of −1 to 1, the dioxolane comprising one selected from the group selected from: 1,3-dioxolane, 4-Methyl-1,3-dioxolane, 2-methyl-1,3-dioxolane, (2-Methyl-1,3-dioxolane-4-yl) methanol, 1,3-Dioxepane, 1,3-Dioxolane-4-methanol, 5-Hydroxy-1,3-dioxane, Glycrol formal mixture (60:40) of 1,3-Dioxolane-4-methanol:5-Hydroxy-1,3-dioxane, 1,4-dioxane, 1,3-dioxolane-2-one, and mixtures thereof.

10. The wipe as claimed in claim 9, wherein the antifungal agent comprises tolnaftate.

11. The wipe as claimed in claim 9, wherein the substrate comprises at least one selected from the group consisting of: creped tissue; un-creped tissue; coform products; hydroentangled webs; air-laid mats; fluff pulp; nonwoven webs; woven webs; composites of any of the previous; lyocell; viscose rayon; blends of lyocell; and blends of viscose rayon.

12. The wipe as claimed in claim 9, wherein the substrate is one of textured or smooth.

13. The wipe claimed in claim 9, wherein the substrate has a basis weight in the range of 40 to 60 grams per square meter.

* * * * *